US006369052B1

(12) United States Patent
Kellar et al.

(10) Patent No.: US 6,369,052 B1
(45) Date of Patent: Apr. 9, 2002

(54) COMBINATION OF HUPERZINE AND NICOTINIC COMPOUNDS AS A NEUROPROTECTIVE AGENT

(75) Inventors: Kenneth J. Kellar, Bethesda, MD (US); Alan P. Kozikowski, Princeton, NJ (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/910,819

(22) Filed: Jul. 23, 2001

Related U.S. Application Data
(60) Provisional application No. 60/223,605, filed on Aug. 7, 2000, and provisional application No. 60/241,670, filed on Oct. 18, 2000.

(51) Int. Cl.$^7$ .......................... A61K 31/55; A61K 31/44; A61K 31/665; A61K 31/435

(52) U.S. Cl. ........................ 514/221; 514/286; 514/290; 514/295; 514/339; 514/343

(58) Field of Search ................................ 514/221, 286, 514/290, 295, 339, 343

(56) References Cited

U.S. PATENT DOCUMENTS

| | | |
|---|---|---|
| 4,929,731 A | 5/1990 | Kozikowski et al. |
| 5,104,880 A | 4/1992 | Kozikowski |
| 5,106,979 A | 4/1992 | Kozikowski et al. |
| 5,177,082 A | 1/1993 | Yu et al. |
| 5,547,960 A | 8/1996 | Kozikowski et al. |
| 5,663,344 A | 9/1997 | Kozikowski et al. |
| 5,869,672 A | 2/1999 | Kozikowski et al. |
| 5,929,084 A | 7/1999 | Zhu et al. |

OTHER PUBLICATIONS

Akaike et al., 1994, "Nicotine induced protection of cultured cortical neurons against N–methyl–D–aspartate receptor–mediated glutamate cytotoxicity", Brain Res. 644:181–187.
Akaike et al., 1994, "Regulation by neuroprotective factors of NMDA receptor mediated nitric oxide synthesis in the brain and retina", Prog Brain Res. 103:391–403.
Arneric et al., 1994, "Nicotinic agonists in Alzheimers disease: does the molecular diversity of nicotine receptors offer the opportunity for developing CNS–selective cholinergic channel activators?", Recent Advances in the Treatment of Neurodegenerative Disorders and Cognitive Dysfunction.
Arneric et al., 1994, "(S)–3–Methyl–5–(1–Methyl–2– Pyrrolidinyl) Isoxazole (ABT 418): A Novel Cholinergic Ligand with Cogniton–Enhancing and Anxiolytic Activities", J. of Pharmacology and Exp. Ther. 270:310–318.
Ayer et al., 1989, "Some new Lycopodium alkaloids", Can. J. Chem. 67;1077–1086.
Ayer et al., 1989,"Alkaloids of Lycopodium selago. On the identity of selagine with huperzine A and the structure of a related alkaloid", Can. J. Chem. 67: 1538–1540.
Bai et al., 1993, "Traditional Chinese medicines and New drug development", Pure and Appl. Chem. 65:1103–1112.
Choi et al., 1989, "Aspartate Neurotoxicity on Cultured Cortical Neurons", J. of Neuroscience Res. 23:116–121.
Choi et al., 1993, "Calcium and Excitotoxic Neuronal Injury", annals NY Acdemy of Sciences 162–170.
Coyle et al., 1984,. "Alzheimers Disease: A disorder of cortical cholinergic innervation", Science 219:1184–1190.
Decker et al., 1994, "(S)–3–Methyl–5–(1–Methyl–2– Pyrrolidinyl) Isoxazole (ABT 418): A novel cholinergic ligand with cognition enhancing and anxiolytic activities: II. In vivo characterization", J. of Pharmacology and Exp. Ther 270:319–328.
Decket et al, 1992, "Effects of nicotine on spatial memory deficits in rats with septal lesions", Brain Res. 572:281–285.
Gordon et al., 1997, "Huperzine–A(HUP–A) Interacts with the NMDA Receptor Ion Channel", FASEB Journal, Core Abstracts, 11(9):268.
Harsing et al., 1992, "Dopamine Efflux from Striatum After Chronic Nicotine: Evidence for Autoreceptor Desensitization", J. of Neurochem. 59(1):48–54.
Hartley et al., 1989, "Delayed Rescue of N–Methyl–D–Aspartate Receptor Mediated Neuronal Injury in Cortical Culture", J. of Pharmacology and Exp. Ther. 250:752–758.
Kaneko et al., 1997, "Nicotine protects cultured cortical neurons against glutamate induced cytotoxicity via $\alpha_{-7}$neuronal receptors and neuronal CNS receptors", Brain Res. 765:135–140.
Kozikowski and Tuckmantel, 1999, "Chemistry, Pharmacology, and Clinical Efficacy of the Chinese Nootropic Agent Huperzine A", Acc. Chem. Res. 32:641–650.
Ladner et al., 1998, "Pharmacological Drug Treatment of Alzheimer Diseasse: The Cholinergic Hypothesis Revisited", J. of Neuropathology and Exp. Neurology 5798):719–731.
Linville et al., 1993, "Nicotinic Agonists Modulate Basal Forebrain Control of Cortical Cerebral Blood Flow in Anesthetized Rats", J. of Pharmacology and Exp. Ther. 267:441–447.

(List continued on next page.)

Primary Examiner—Raymond Henley, III
(74) Attorney, Agent, or Firm—Pennie & Edmonds LLP

(57) ABSTRACT

The present invention provides compositions and methods for treating, preventing, or reversing neuronal dysfunction including cognitive decline, such as cognitive decline associated with aging and minimal cognitive impairment; severe neurodegenerative disorders, such as Alzheimer's disease; and neuronal dysfunction associated with loss of motor skills, such as Parkinson's disease and amyotrophic lateral sclerosis. The compositions and methods of the invention can also treat or prevent neuronal dysfunction resulting from CNS injury, such as stroke, spinal-cord injury, and peripheral-nerve injury. The compositions of the invention comprises a huperzine compound and a nicotinic compound.

58 Claims, 3 Drawing Sheets

OTHER PUBLICATIONS

Figure 2B:
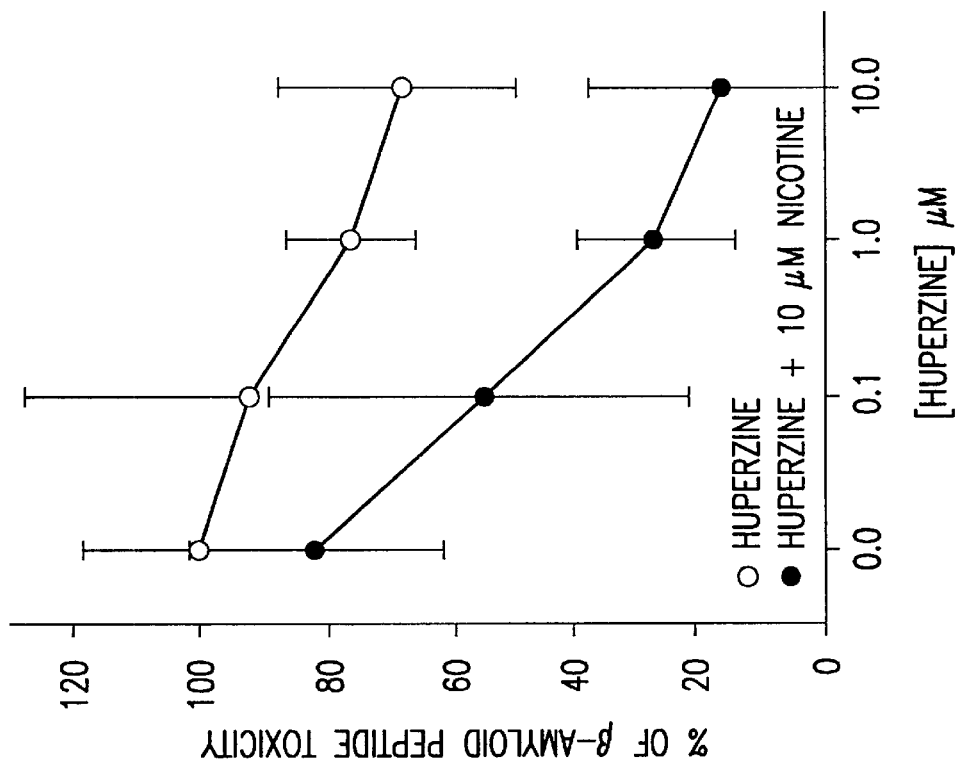

Liu et al., 1986, "The Structures of Huperzine A and B two new alkaloids exhibiting marked anticholinesterase activity", Can. J. Chem. 6 4:837–839.

Marin et al., 1994, "Nicotine protects cultured striatal neurones against N–methly–D–aspartate receptor–mediated neurotoxicity", NeuroReport 5:1977–1980.

Mattson et al., 1988, "Neurotransmitters in the regulation of neuronal cytoarchitecture", Brain Res. Reviews 13:179–212.

Meldrum and Garthwaite, 1990, "Excitatory amino acid neurotoxicity and neurodegenerative disease", TIPS 11:379–387.

Sahaklan et al., 154, "The Effects of Nicotine on Attention, Information Processing, and Short Term Memory in Patients with Demential of the Alzheimer Type", British J. of Psychiatry 154:797–800.

Sanberg et al., 1993, "Nicotine Potentiation of Haloperidol–Induced Catalepsy: Striatal Mechanisms", Pharmacology Biochem. And Behavior 46:303–307.

Sjak–Shie et al., 1991, "Some Novel Actions of Nicotine in Nucleus Basalis Lesioned Rats and in Hippocampal Slices", Cholinergic Basis for Alzheimer Therapy 379–385.

Sullivan et al., 1995, "Cholinergic Channel Activators: Novel Opportunities for the Treatment of CNS Disorders", Proc. West. Pharmacol. Soc. 38:127–130.

Ved et al., 1997, "Huperzine A, a potential therapeutic agent for dementia, reduces neuronal cell death caused by glutamate", Medicinal Chem. 8(43):963–968.

Wesnes et al., 1984, "Effects of Scopolamine and nicotine on human rapid information processing perfromance", Psychopharmacology 82:147–150.

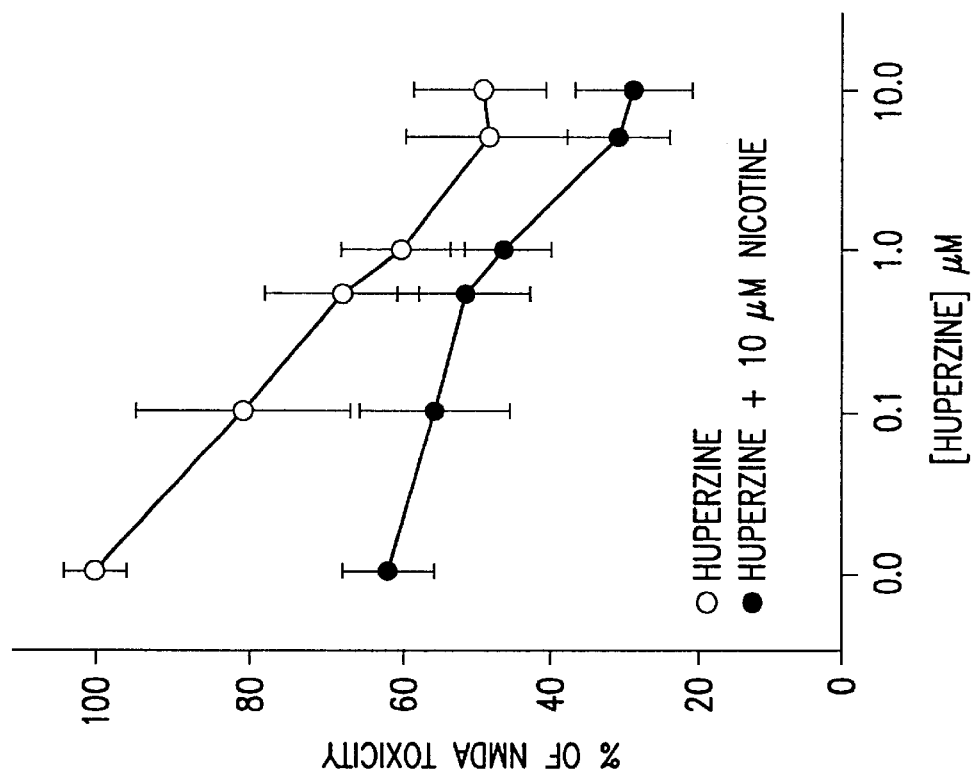
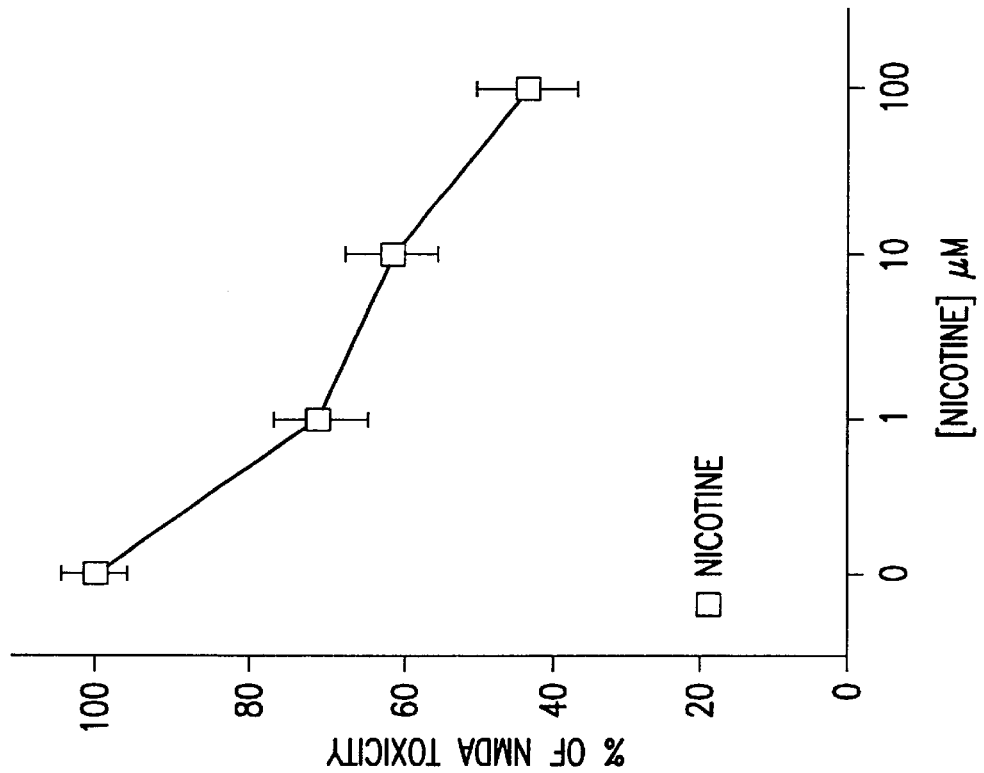

COMBINATION OF HUPERZINE AND NICOTINIC COMPOUNDS AS A NEUROPROTECTIVE AGENT

This application claims the benefit of U.S. Provisional Application No. 60/223,605, filed Aug. 7, 2000, hereby incorporated herein by reference in its entirety and U.S. Provisional Application No. 60/241,670, filed Oct. 18, 2000, hereby incorporated herein by reference in its entirety.

This invention was made in part under Department of Army Grant No. DAMD 17-99-2-9907.

1. FIELD OF THE INVENTION

The present invention relates to compositions comprising huperzine compounds and nicotinic compounds and to methods of using huperzine compounds and nicotinic compounds in combination to provide a neuroprotective effect.

2. BACKGROUND OF THE INVENTION

Neuronal dysfunction includes cognitive decline, which is characterized by concentration loss, memory-acquisition loss, and information-storage or retrieval loss. Neuronal dysfunction can also result from central nervous system ("CNS") injury, such as stroke, spinal-cord injury, and peripheral-nerve injury. Cognitive decline is symptomatic of neuronal disorders, such as cognitive decline associated with aging and minimal cognitive impairment (also known as minimal cognitive disorder) as well as severe neurodegenerative disorders, such as Alzheimer's disease. Neuronal dysfunction is also associated with disorders that result in loss of motor skills, such as Parkinson's disease and amyotrophic lateral sclerosis. It is thought that degeneration of the central cholinergic system contributes to cognitive decline.

For example, there is much evidence indicating that the memory and attention deficits in patients with Alzheimer's disease are due to degeneration of cholinergic systems that originate in the basal-forebrain-cholinergic system and innervate the neocortex, hippocampus and other brain areas (Coyle et al., 1983, *Science* 219:1184.) Additional evidence suggests that nicotinic acetylcholine receptors ("nAChR") play a role in cholinergic dysfunction, and nicotine and its analogs can affect these dysfunctions. Nicotine activates nAChR, eliciting a number of functional responses, including neurotransmitter release and neurogenic control of cerebral blood flow (S. P. Arneric and M. Williams, 1994, *Recent Advances In the Treatment of Neurodegenerative Disorders and Cognitive Function* p 58; Linville et al., 1993, *J. Pharmacol. Exp. Ther.* 267:440).

Nicotine improves information processing and attention in patients with Alzheimer's type dementia, as well as the performance of cognitively demanding tasks in healthy human adult subjects (Sahakian et al., 1989, *Br. J. Psychiatry* 154:797; Wesnes et al., 1984, *Psychopharmacology* 82:147). Nicotine has also been shown to improve learning and memory performance and to reverse deficits in models of impaired-cognitive performance (Decker, 1992, *Brain Res.* 572:281). In animal models of cholinergic disturbance produced by NBM lesions, chronic pretreatment with nicotine reduced cell loss in the neocortex (Sjak-Shie et al., 1991, in *Cholinergic Basis for Alzheimer Therapy*, pp. 379). Analogs of nicotine can similarly exhibit neuroprotective and cognitive-enhancing properties (Sullivan et al., 1995, *Proc. West. Pharmacol. Soc.* 38:127; Arneric et al., 1994, *J. Pharmacol. Exp. Ther.* 270:310; Decker et al., 1994, *J. Pharmacol. Exp. Ther.* 270:318).

Cortical neurodegeneration in some neuropathies (e.g., stroke, ischemia, etc.) has been attributed to glutamate binding to N-methyl-D-aspartate ("NMDA") receptors, which play a crucial role in glutamate-induced neurodegeneration (Mattson, 1988, *Brain Res.* 13:174; Choi et al., 1989, *J. Neurosci. Res.* 23:116; Hartley & Choi, 1989, *J. Pharmacol. Exp. Ther.* 250:752; Meldrum & Garthwaire, 1990, *Trends Pharmacol. Sci.* 11:379). For example, symptoms of neuronal damage caused by organophosphate ("OP") toxicity (i.e. tremors, seizures or convulsions) have been partially attributed to the release of large quantities of glutamate during OP intoxication. The released glutamate causes activation of NMDA receptors and increases $Ca^{2+}$ influx that in turn causes persistent elevation in $Ca^{2+}$ concentrations, eventually resulting in neuronal death (Ved et al., 1997, *Neuroreport* 8:963; Choi, 1994, *Ann. NY Acad. Sci.* 747:162). Nicotine protects cultured cortical neurons against NMDA receptor-mediated, glutamate-induced cell death (Marin et al., 1994, *Neuropharmacology and Neurotoxicology* 5:1977; Kaneko et al, 1997, *Brain Research* 765:135. Akaike et al., 1994, *Prog. Brain Res.* 130:391).

Administration of acetylcholinesterase ("AChE") inhibitors such as tacrine, donepezil, and others have proven useful in the treatment of Alzheimer's disease. Two relatively new lycopodium alkaloids, (−)-huperzine A and B, isolated from Huperzia serrata (Thunb.) Trev., a Chinese folk medicine, appear superior to these and other compounds such as tacrine and physostigmine (U.S. Pat. No. 5,177,082 to Yu et al.; Liu et al., 1986, *Can. J. Chem.* 64:837; Ayer et al., 1989, *Can. J. Chem.* 67:1077; Ayer et al., 1989, *Can. J Chem.* 67:1548). The structures of huperzine A and huperzine B are shown in J. Liu et al., *Can. J. Chem.* 64:837–839 (1986), incorporated herein by reference. The structures of (−)-huperzine A and (−)-huperzine B are depicted below.

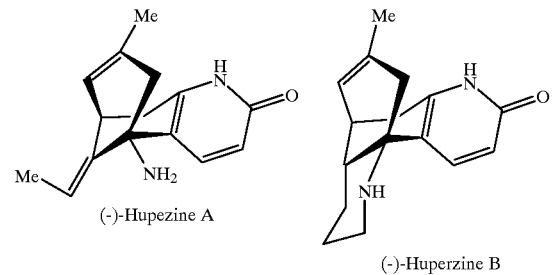

(−)-Hupezine A (−)-Huperzine B

Huperzine has been shown to ameliorate the memory loss associated with Alzheimer's disease (Kozikowski et al., 1999, *Acc. Chem. Res.*, 32:641). And, like nicotine, huperzine A significantly reduces the neuronal-cell death caused by glutamate. In addition, the neuroprotective effect of huperzine A against glutamate increases with age. Ved et al., 1997, *Neuroreport* 8:963.

Other clinical and histopathological findings of Alzheimer's disease include formation of paired helical filaments and amyloid plaques, along with increased formation of amyloid protein. In artificial lipid bilayers, amyloid proteins have been shown to form cation channels that conduct calcium and other ions. The resulting ion fluxes could be homeostatically catastrophic if such channels are expressed in cells, supporting the concept that cell death in Alzheimer's disease can be partly the result of amyloid channel activity. This theory is supported by the finding that β-amyloid peptide is toxic to neurons. Nicotine protects against this toxicity.

The compounds currently in clinical use for treating or ameliorating neuronal dysfunction have significant side effects. Huperzine has been used for many years as a Chinese herbal remedy for alleviating memory problems (Kozikowski, 1999, *Acc. Chem. Res.* 32:641; Bai, 1993, *Pure Appl. Chem.* 65:1103). Nonetheless, there remains a need in the art for additional and more effective therapies that treat, prevent, or reverse neuronal dysfunction, such as cognitive decline characterized by concentration loss; memory-acquisition loss; information-storage or retrieval loss; neuronal disorders such as cognitive decline associated with aging and minimal cognitive impairment; severe neurodegenerative disorders such as Alzheimer's disease; neuronal dysfunction associated with loss of motor skills, such as Parkinson's disease and amyotrophic lateral sclerosis; neuronal dysfunction resulting from CNS injury such as stroke, spinal-cord injury, and peripheral-nerve injury. There is a particular need for additional and more effective therapies that treat, prevent, or reverse Alzheimer's disease and minimal cognitive impairment.

Citation or identification of any reference in Section 2 of this application is not an admission that such reference is prior art to the present invention.

3. SUMMARY OF THE INVENTION

In one embodiment, the present invention provides a composition comprising a huperzine compound or pharmaceutically acceptable salt or hydrate thereof and a nicotinic compound or pharmaceutically acceptable salt or hydrate thereof. The composition can further include a pharmaceutically acceptable carrier, diluent or excipient, and can be administered to an animal subject, including a human, in connection with the methods of the invention to treat, prevent, or reverse neuronal dysfunction. Examples of neuronal dysfunction treated, prevented, or reversed using the compositions of the invention include, but are not limited to, cognitive decline characterized by concentration loss; memory-acquisition loss; information-storage or retrieval loss; neuronal disorders such as cognitive decline associated with aging and minimal cognitive impairment; severe neurodegenerative disorders such as Alzheimer's disease; and neuronal dysfunction associated with loss of motor skills, such as Parkinson's disease and amyotrophic lateral sclerosis. The compositions of the invention can also be used to treat, prevent, or reverse neuronal dysfunction resulting from CNS injury such as stroke, spinal-cord injury, and peripheral-nerve injury. The compositions of the invention are particularly useful for treating, preventing, or reversing Alzheimer's disease and minimal cognitive impairment.

In a separate embodiment, the compositions of the invention are formulated in a patch for transdermal administration.

In another embodiment, the invention comprises a method of providing neuroprotection in a subject, said method comprising adjunctively administering to a subject in need thereof a huperzine compound or a pharmaceutically acceptable salt or hydrate thereof and a nicotinic compound or pharmaceutically acceptable salt or hydrate thereof in amounts effective to provide neuroprotection.

In still another embodiment, the invention relates to a method for treating, preventing, or reversing a neuronal dysfunction, comprising adjunctively administering to a patient in need thereof effective amounts of a huperzine compound, pharmaceutically acceptable salt or hydrate thereof and a nicotinic compound, pharmaceutically acceptable salt or hydrate thereof.

The methods of the invention preferably provide a prophylactic or therapeutic neuroprotective effect. For example, the invention provides methods of treating, preventing, or reversing neuronal dysfunction. Examples of neuronal dysfunction treated, prevented, or reversed using the methods of the invention include, but are not limited to, cognitive decline characterized by concentration loss; memory-acquisition loss; information-storage or retrieval loss; neuronal disorders such as cognitive decline associated with aging and minimal cognitive impairment; severe neurodegenerative disorders such as Alzheimer's disease; and neuronal dysfunction associated with loss of motor skills such as Parkinson's disease and amyotrophic lateral sclerosis. The methods of the invention can also be used to treat, prevent, or reverse neuronal dysfunction resulting from CNS injury such as stroke, spinal-cord injury, and peripheral-nerve injury.

In still another embodiment, the invention comprises a method of providing neuroprotection, comprising contacting a neuron with a huperzine compound or pharmaceutically acceptable salt or hydrate thereof and a nicotinic compound or pharmaceutically acceptable salt or hydrate thereof in amounts effective to provide neuroprotection.

The present invention may be understood more fully by reference to the following figures, detailed description and illustrative examples, which are intended to exemplify non-limiting embodiments of the invention.

4. BRIEF DESCRIPTION OF THE FIGURES

FIG. 1A and FIG. 1B illustrate the synergistic neuroprotective effects of (−)-nicotine and (−)-huperzine A against NMDA toxicity in mixed cortical cultures from mouse brain. Graph A represents the dose-dependent effect of (−)-nicotine alone. Graph B represents the dose-dependent effect of (−)-huperzine A alone (unfilled circles) and in the presence (filled circles) of 10 $\mu$M (−)-nicotine. Toxicity was induced by a 10 minute treatment with 75 $\mu$M NMDA in the absence or presence of the indicated drugs.

Figure 2A:
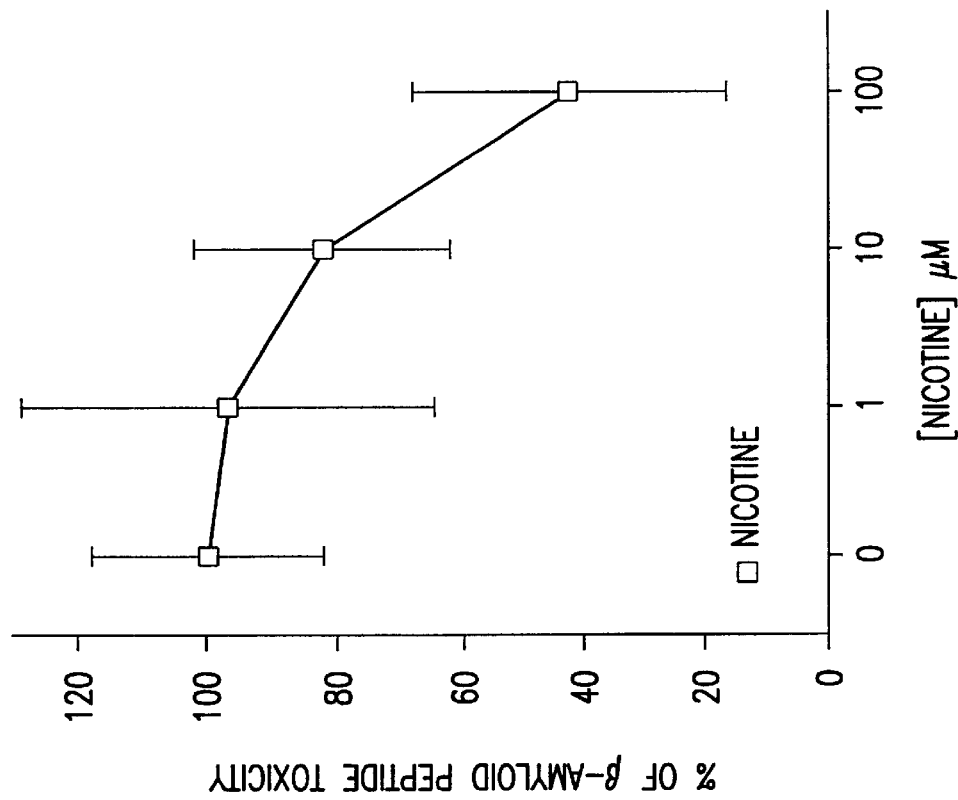

FIG. 2A and FIG. 2b illustrate the synergistic neuroprotective effects of (−)-nicotine and (−)-huperzine A against $\beta$-amyloid peptide toxicity in cultures of cerebellar neurons from mouse brain. Graph A represents the dose-dependent effect of (−)-nicotine alone. Graph B represents the dose-dependent effect of (−)-huperzine A alone (unfilled circles) and in the presence (filled circles) of 10 $\mu$M nicotine. Toxicity was induced by a 48 hour treatment with 25 $\mu$M $\beta$-amyloid peptide in the absence or presence of the indicated drugs.

Figure 3:
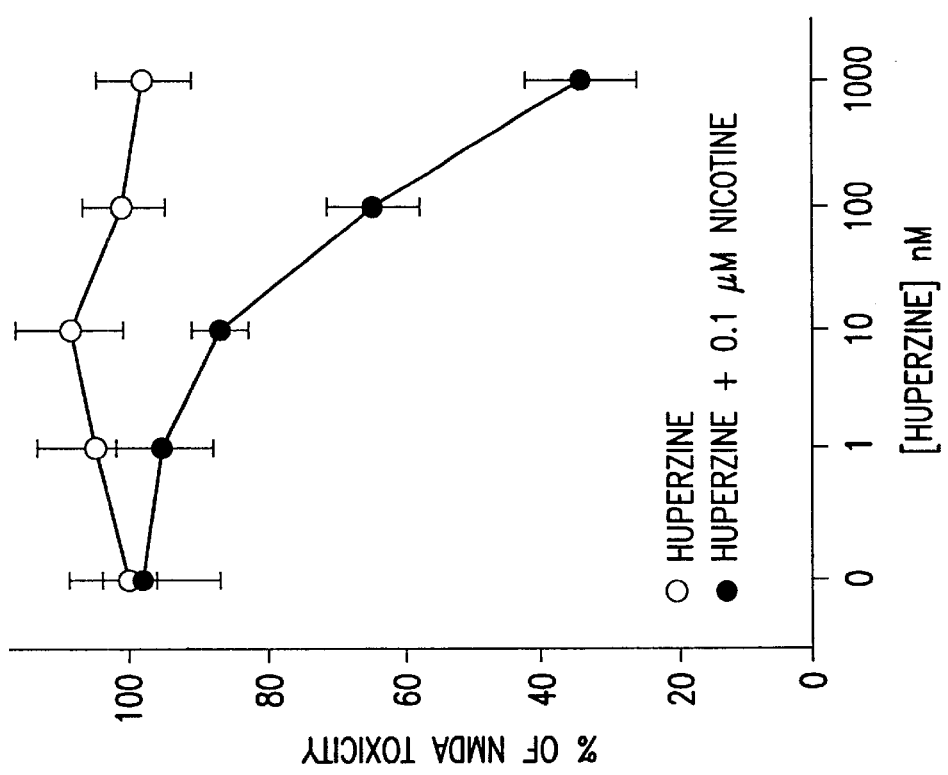

FIG. 3 illustrates the synergistic neuroprotective effect of (−)-nicotine and (−)-huperzine A against NMDA toxicity in mixed cortical cultures from mouse brain. The graph represents the dose-dependent effect of (−)-huperzine A alone and in the presence of 0.1 $\mu$M (−)-nicotine. Toxicity was induced by a 10 minute treatment with 75 $\mu$M NMDA in the absence or presence of the indicated drugs.

5. DETAILED DESCRIPTION OF THE INVENTION

5.1 Definitions

As used herein, the following terms shall have the following meanings.

As used herein, the phrase "huperzine compound" includes huperzine A and huperzine B, analogs of huperzine A and huperzine B, derivatives of huperzine A and huperzine B and salts and hydrates thereof. The term "huperzine compound" also encompasses all homologs, positional isomers, and all stereoisomers and mixtures of stereoisomers in optically active or racemic form of huperzine A and huperzine B and salts and hydrates thereof.

According to the invention, analogs and derivatives of huperzine A or huperzine B respectively have the generic chemical structures A and B below:

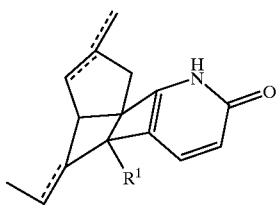

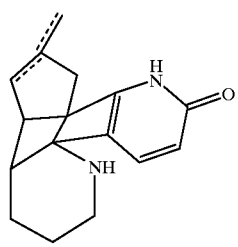

where $R^1$ represents $NH_2$ or a suitable substituent as defined below and the dotted line represents the optional presence of a carbon-carbon bond that, when present, completes a carbon-carbon double bond. In addition, an analog or derivative of huperzine A or huperzine B will have neuroprotective activity when tested as set forth in Examples 6.1 or 6.2 described below. Thus one of skill in the art can readily identify analogs and derivatives of huperzine suitable for use with invention by obtaining compounds with core structures A and B as set forth in section 5.4 below and testing those compounds for neuroprotective activity as set forth in Examples 6.1 or 6.2 below.

Examples of huperzine compounds include, but are not limited to, the huperzine analogs of structure IV depicted at column 2, lines 21–59 of Pat. No. 4,929,73 1; column 3, lines 1–39 of U.S. Pat. No. 5,106,979; column 2, lines 30–61 of U.S. Pat. No. 5,663,344; and column 2, lines 29–61 of U.S. Pat. No. 5,869,672; dihydro-desmethyl-huperzine, 11-desmethyl-11-chloro-huperzine A, and the compounds of structure I depicted at column 2, lines 8–62 of U.S. Pat. No. 5,104,880; the compounds of structures I, II, and III depicted at column 1, lines 15–51 of U.S. Pat. No. 5,177,082; the huperzine derivatives of structure II depicted at column 2, line 1 to column 4, line 6 of U.S. Pat. No. 5,929,084; and the huperzine analogs of structure I depicted at column 2, lines 18–40 of U.S. Pat. No. 5,547,960, all of which patents are hereby incorporated herein by reference.

Preferred among these various huperzine compounds are huperzine A and huperzine B, including (−)-huperzine A, (+)-huperzine A, (±)-huperzine A, (−)-huperzine B, (+)-huperzine B, and (±)-huperzine B, particularly (−)-huperzine A and (±)- huperzine A, and the C-10 huperzine analogs described in U.S. Pat. No. 5,547,960, particularly the (+), (−) and (±) forms, and especially the (+), (−) and (±) forms of 10,10-dimethyl huperzine A and 10-methyl huperzine A.

As used herein, the phrase "nicotinic compound" means any chemical compound that is an agonist of the nicotinic-acetylcholine-receptor family and that stimulates the receptor such that the receptor channel is opened and ions (i.e., sodium, potassium, and calcium ions) can flow down their concentration gradients. Such compounds can be identified by well-know assays and methods (see, e.g. Xiao et al., 1998, *Mol. Pharmacol.* 54:322; Zhang et al., 1999, *Mol. Pharmacol.* 55:970–981; Sackmann, 1992, *Science* 256:503–512; see generally, Goodman & Gillman's The Pharmacological Basis of Therapeutics pp. 178–179 (Joel G. Hardman et al. eds., 9th ed. 1996)) all of which citations are hereby incorporated herein by reference in their entirety. The phrase "nicotinic compound" encompasses nicotine, analogs of nicotine, derivatives of nicotine and salts and hydrates thereof. The term "nicotinic compound" also encompasses all homologs, positional isomers, and all stereoisomers and mixtures of stereoisomers in optically active or racemic form of nicotine and salts and hydrates thereof. The term "nicotinic compound" also encompasses epibatidine, cytisine, lobeline, and anabasine and analogs and derivatives thereof, and all homologs, positional isomers, and all stereoisomers and mixtures of stereoisomers in optically active or racemic form of epibatidine, cytisine, lobeline, and anabasine and salts and hydrates thereof.

According to the invention, analogs and derivatives of nicotine have the generic chemical structure C below:

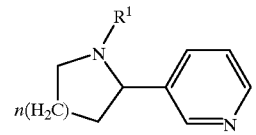

where $R^1$ is a $(C_1–C_6)$alkyl or a suitable substituent as defined below, preferably, $(C_1–C_6)$alkyl and n is an integer ranging from 1 to 3. In addition, an analog or derivative of nicotine will have neuroprotective activity when tested as set forth in Examples 6.1 or 6.2 described below. Thus, one of skill in the art can readily identify analogs and derivatives of nicotine suitable for use with invention by obtaining compounds with the structure C as set forth in section 5.4 below and testing those compounds for neuroprotective activity as set forth in Examples 6.1 or 6.2 below.

Useful nicotinic compounds include, but are not limited to, nicotine (Gattermann & Wieland, *Laboratory Methods of Organic Chemistry*, 24th ed., 1937); anabaseine, myosmine, anatabine, the nicotinic analogs of structure I depicted at column 15, lines 25–34 of U.S. Pat. No. 5,840,906, and the nicotinic analogs described at column 2, line 35 to column 4, line 10 of U.S. Pat. No. 5,276,043; lobeline (H. Wieland, Ber. 1921, 54:1784); the lobeline analogs of structure I depicted at column 5, line 53 to column 6, line 22 of U.S. Pat. 5,830,904; the nicotine analogs described at column 4, lines 1–14 of U.S. Pat. No. 5,691,365; the aryl substituted olefinic secondary amine compounds described at column 4, lines 9–44 of U.S. Pat. No. 5,663,356; the nicotinic analogs of structure I depicted at column 7, lines 1–31 of U.S. Pat. No. 5,278,176; the nicotinic derivatives of structure IV depicted at column 2, lines 38–46 of U.S. Pat. No. 4,965, 074; anabasine (Sadykov & Timbekov, 1956, *J. Appl. Chem USSR* 29:148); epibatidine (Spande et al., 1992, *J. Am. Chem. Soc.* 114:3475); cytisine (Ing, *J. Chem Soc.* 1931:2200); lobeline (Weiland & Dragendorff, 1929, Ann. 473:83) and other lobelia alkaloids, including lobelanidine (Weilan et al., 1925, Ann 444:40) and lobelanine (Weilan et al., 1925, Ann. 44:25), all which patents and references are hereby incorporated herein by reference. Preferred among the various nicotinic compounds are (−), (+), and (±) nicotine, epibatidine, cytisine, lobeline, and anabasine and all stereoisomers, mixtures of stereoisomers, and optically active forms thereof.

The phrase "compound of the invention" means a huperzine compound, a pharmaceutically acceptable salt thereof or hydrate thereof, or a nicotinic compound or pharmaceutically acceptable salt thereof or hydrate thereof.

The phrase "composition of the invention" means a composition comprising a huperzine compound, pharmaceutically acceptable salt thereof or hydrate thereof and a nicotinic compound, pharmaceutically acceptable salt thereof or hydrate thereof. Preferably, compositions of the invention are pharmaceutical compositions comprising a huperzine compound, pharmaceutically acceptable salt thereof or hydrate thereof and a nicotinic compound, pharmaceutically acceptable salt thereof or hydrate thereof, in neuroprotective amounts, and a pharmaceutically acceptable vehicle, carrier, or delivery system. A pharmaceutically acceptable vehicle or carrier can comprise a carrier, excipient, diluent, or a mixture thereof. The phrase "neuroprotective amount" means the amount of a huperzine compound, pharmaceutically acceptable salt thereof or hydrate thereof and a nicotinic compound, pharmaceutically acceptable salt thereof or hydrate thereof that can elicit a neuroprotective response in a subject.

The term "analog" refers to a chemical compound that is structurally similar to a parent compound and has chemical properties or pharmaceutical activity in common with the parent compound. Analogs include, but are not limited to, homologs, i.e., where the analog differs from the parent compound by one or more carbon atoms in series; positional isomers; compounds that differ by interchange of one or more atoms by a different atom, for example, replacement of a carbon atom with an oxygen, sulfur, or nitrogen atom; and compounds that differ in the identity one or more functional groups, for example, the parent compound differs from its analog by the presence or absence of one or more suitable substituents. Suitable substituents include, but not limited to, $(C_1-C_8)$alkyl; $(C_1-C_8)$alkenyl; $(C_1-C_8)$alkynyl: aryl; $(C_2-C_5)$heteroaryl; $(C_1-C_6)$heterocycloaklyl; $(C_3-C_7)$ cycloalkyl; O—$(C_1-C_8)$alkyl; O—$(C_1-C_8)$alkenyl; O—$(C_1-C_8)$alkynyl; O-aryl; CN; OH; oxo; halo, C(O)OH; COhalo; O(CO)halo; $CF_3$, $N_3$; $NO_2$, $NH_2$; NH($(C_1-C_8)$ alkyl); N($(C_1-C_8)$alkyl)$_2$; NH(aryl); N(aryl)$_2$ N($(C_1-C_8)$ alkyl)(aryl); C(O)NH$_2$; C(O)NH($(C_1-C_8)$alkyl); C(O)N $((C_1-C_8)$alkyl)$_2$; C(O)NH(aryl); C(O)N(aryl)$_2$; O(CO)NH$_2$; NHOH; NOH($(C_1-C_8)$alkyl); NOH(aryl);O(CO)NH($(C_{1-8})$ alkyl); O(CO)N($(C_1-C_8)$alkyl)$_2$; O(CO)NH(aryl); O(CO)N (aryl)$_2$; CHO; CO($(C_1-C_8)$alkyl); CO(aryl); C(O)O($(C_1-C_8)$ alkyl); C(O)O(aryl); O(CO)($(C_1-C_8)$alkyl); O(CO)(aryl); O(CO)O($(C_1-C_8)$alkyl); O(CO)O(aryl); S—$(C_1-C_8)$alkyl; S—$(C_1-C_8)$alkenyl; S—$(C_1-C_8)$alkynyl; S-aryl; S(O)—$(C_1-C_8)$alkyl; S(O)—$(C_1-C_8)$alkenyl; S(O)—$(C_1-C_8)$ alkynyl; and S(O)-aryl; S(O)$_2$—$(C_1-C_8)$alkyl; S(O)$_2$—$(C_1-C_8)$alkenyl; S(O)$_2$—$(C_1-C_8)$alkynyl; and S(O)$_2$-aryl. One of skill in art can readily choose a suitable substituent based on the stability and pharmacological activity of the compound of the invention.

The term "alkyl" means a saturated, monovalent, unbranched or branched hydrocarbon chain. Examples of alkyl groups include, but are not limited to, $(C_1-C_8)$alkyl groups, such as methyl, ethyl, propyl, isopropyl, 2-methyl-1-propyl,2-methyl-2-propyl,2-methyl-1-butyl,3-methyl-1-butyl,2-methyl-3-butyl,2,2-dimethyl-1-propyl, 2-methyl-1-pentyl,3-methyl-1-pentyl,4-methyl-1-pentyl,2-methyl-2-pentyl,3-methyl-2-pentyl, 4-methyl-2-pentyl,2,2-dimethyl-1-butyl,3,3-dimethyl-1-butyl,2-ethyl-1-butyl, butyl, isobutyl, t-butyl, pentyl, isopentyl, neopentyl, and hexyl, heptyl, and octyl. An alkyl group can be unsubstituted or substituted with one or two suitable substituents.

The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to $(C_2-C_8)$alkenyl groups, such as vinyl, allyl, butenyl, pentenyl, hexenyl, butadienyl, pentadienyl, hexadienyl, 2-ethylhexenyl,2-propyl-2-butenyl,4-(2-methyl-3-butene)-pentenyl. An alkenyl group can be unsubstituted or substituted with one or two suitable substituents.

The term "alkynyl" means monovalent, unbranched or branched hydrocarbon chain having one or more triple bonds therein. The triple bond of an alkynyl group can be unconjugated or conjugated to another unsaturated group. Suitable alkynyl groups include, but are not limited to, $(C_2-C_8)$alkynyl groups, such as ethynyl, propynyl, butynyl, pentynyl, hexynyl, methylpropynyl, 4-methyl-1-butynyl,4-propyl-2-pentynyl, and 4-butyl-2-hexynyl. An alkynyl group can be unsubstituted or substituted with one or two suitable substituents.

The term "aryl" means a monocyclic or polycyclic-aromatic group comprising carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or two suitable substituents. Preferably, the aryl group is a monocyclic ring, wherein the ring comprises 6 carbon atoms, referred to herein as "$(C_6)$aryl".

The term "heteroaryl" means a monocyclic- or polycyclic aromatic ring comprising carbon atoms, hydrogen atoms, and one or more heteroatoms, preferably, 1 to 3 heteroatoms, independently selected from nitrogen, oxygen, and sulfur. As well known to those skilled in the art, heteroaryl rings have less aromatic character than their all-carbon counter parts. Thus, for the purposes of the invention, a heteroaryl group need only have some degree of aromatic character. Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, phenyl, isoxazolyl, and oxazolyl. A heteroaryl group can be unsubstituted or substituted with one or two suitable substituents. Preferably, a heteroaryl group is a monocyclic ring, wherein the ring comprises 2 to 5 carbon atoms and 1 to 3 heteroatoms, referred to herein as "$(C_2-C_5)$heteroaryl".

The term "cycloalkyl" means a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, $(C_3-C_7)$cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Preferably, the cycloalkyl group is a monocyclic ring or bicyclic ring.

The term "heterocycloalkyl" means a non-aromatic monocyclic or polycyclic ring comprising carbon and hydrogen atoms and at least one heteroatom, preferably, 1 to 4 heteroatoms selected from nitrogen, oxygen, and sulfur. A heterocycloalkyl group can have one or more carbon-carbon double bonds or carbon-heteroatom double bonds in the ring as long as the ring is not rendered aromatic by their presence.

Examples of heterocycloalkyl groups include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl. A heterocycloalkyl group can be unsubstituted or substituted with one or two suitable substituents. Preferably, the heterocycloalkyl group is a monocyclic or bicyclic ring, more preferably, a monocyclic ring, wherein the ring comprises from 2 to 6 carbon atoms and form 1 to 3 heteroatoms, referred to herein as ($C_1$–$C_6$)heterocycloalkyl.

The term "halogen" means fluorine, chlorine, bromine, or iodine. Correspondingly, the term "halo" means fluoro, chloro, bromo, and iodo.

The term "derivative" refers to an analog, as defined above, that is synthesized in one or more chemical reactions from its parent compound.

The phrase "adjunctively administering" means administering a huperzine compound and a nicotinic compound to a subject in a sequence and within a time interval such that they can act together to treat, prevent, or reverse neuronal dysfunction. For example, the compounds of the invention can be administered simultaneously in the same or separate compositions. When administered in separate compositions, a different administration mode can be used for each composition. The compounds of the invention can be administered sequentially in any order at different points in time.

The phrase "pharmaceutically acceptable salt(s)," as used herein includes, but is not limited to, salts of acidic or basic groups that may be present in the huperzine compounds, nicotinic compounds and hydrates thereof. Huperzine compounds, nicotinic compounds, and hydrates thereof that are basic in nature are capable of forming a wide variety of salts with various inorganic and organic acids. The acids that may be used to prepare pharmaceutically acceptable salts of such basic compounds are those that form salts comprising pharmacologically acceptable anions including, but not limited to, acetate, benzenesulfonate, benzoate, bicarbonate, bitartrate, edetate, camsylate, carbonate, bromide, chloride, iodide, citrate, dihydrochloride, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate (i.e., 1,1'-methylene-bis-(2-hydroxy-3-naphthoate)). Huperzine compounds, nicotinic compounds, and hydrates thereof that include an amino moiety can also form pharmaceutically acceptable salts with various amino acids, in addition to the acids mentioned above. Huperzine compounds, nicotinic compounds, and hydrates thereof that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein, the term "hydrate" means a huperzine compound, nicotinic compound, or a pharmaceutically acceptable salt thereof that further includes a stoichiometric or non-stoichiometric amount of water bound to it by non-covalent intermolecular forces.

In one embodiment, "treatment" or "treating" refers to an amelioration, prophylaxis, or reversal of a disease or disorder, or at least one discernible symptom thereof. In another embodiment, "treatment" or "treating" refers to an amelioration, prophylaxis, or reversal of at least one measurable physical parameter, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder, for example, neuronal dysfunction associated with cognitive decline, neuronal dysfunction associated with loss of motor skills, or neuronal dysfunction associated with CNS injury.

In certain embodiments, the compounds of the invention are administered as a preventative measure. As used herein, "prevention" or "preventing" refers to a reduction of the risk of acquiring a given disease or disorder. In a preferred mode of the embodiment, the compounds of the invention are administered as a preventative measure to a subject having a genetic or non-genetic predisposition to neuronal dysfunction, such as cognitive decline even though symptoms of the disorder are absent or minimal.

The term "neuroprotection" as used herein, means treating, preventing, or reversing cognitive decline associated with concentration loss, memory-acquisition loss, and information-storage or retrieval loss including, but not limited to, neuronal disorders, such as cognitive decline associated with aging and minimal cognitive impairment and severe neurodegenerative disorders, such as Alzheimer's disease. The term "neuroprotection" also includes treating, preventing, or reversing neuronal dysfunction associated with loss of motor skills, such as Parkinson's disease and amyotrophic lateral sclerosis as well as neuronal dysfunction resulting from CNS injury, such as stroke, spinal-cord injury, and peripheral-nerve injury.

The term "subject" refers to any animal, preferably a mammal, to which will or has been administered compounds or compositions of the invention to provide a neuroprotective effect. The term "mammal" as used herein, encompasses any mammal. Examples of mammals include, but are not limited to, cows, horses, sheep, pigs, cats, dogs, mice, rats, rabbits, guinea pigs, monkeys, humans etc., more preferably, a human. Preferably, a subject is in need of neuroprotection.

5.2 The Compounds of the Invention

Quite surprisingly, it has now been discovered that nicotinic compounds, pharmaceutically acceptable salts or hydrates thereof can act synergistically with huperzine compounds, pharmaceutically acceptable salts or hydrates thereof to protect CNS cells against cell death induced by excitatory amino acids or β-amyloid. Such neuroprotection can treat, prevent, or reverse neuronal dysfunction, such as cognitive decline characterized by concentration loss, memory-acquisition loss, and information-storage or retrieval loss; neuronal disorders, such as cognitive decline associated with aging and minimal cognitive impairment; severe neurodegenerative disorders, such as Alzheimer's disease; and neuronal dysfunction associated with loss of motor skills, such as Parkinson's disease and amyotrophic lateral sclerosis. Such neuroprotection can also treat, prevent, or reverse neuronal dysfunction resulting from CNS injury, such as stroke, spinal-cord injury, and peripheral-nerve injury. Preferably, the nicotinic compound is nicotine and the huperzine compound is huperzine A. More preferably, the nicotinic compound is (−)-nicotine and the huperzine compound is (−)-huperzine A.

While not intending to be bound by any particular theory of operation, it is believed that the compounds of the invention exert their neuroprotective effects via different pharmacological mechanisms of action. The cognitive neuroprotective effects of nicotine are thought to be associated with a direct action at nicotinic receptors, as well as with the ability of nicotine to release, inter alia, acetylcholine, norepinephrine, dopamine, glutamate, GABA and serotonin from neurons. In contrast, huperzine A is a very potent and selective inhibitor of AChE, with almost no action on butyrylcholinesterase. It has recently been suggested, however, that while huperzine's effects on memory are thought to be related to its AChE-blocking ability, the neuroprotective effects of huperzine and its analogs and derivatives can result, at least partially, from blockade of calcium mobilization through the NMDA receptor (Ved et al., 1997, *Neuroreport* 8:963).

These different pharmacological mechanisms permit the compounds of the invention to act synergistically in two respects. First, adjunctive administration of compounds of the invention allows greater neuroprotection than administration of either compound class alone. Second, adjunctive administration of compounds of the invention permits the same or greater level of neuroprotection using lower dosages. For example, the same or greater level of neuroprotection achieved with 10 units of nicotine or 10 units of huperzine A alone can now be achieved with 5 units of nicotine in combination with 5 units of huperzine A. Achievement of the same or greater neuroprotection using lower compound dosages provides significant benefits and results in fewer adverse or toxic side effects. Thus, owing to the synergistic pharmacological activities of the compounds of the invention, a greater neuroprotection is achieved than when either compound class is administered alone and the same or greater levels of neuroprotection are achieved with fewer adverse side effects.

According to the methods of the invention, the compounds of the invention are adjunctively administered to a subject, especially a human, in amounts effective to provide a therapeutic or prophylactic neuroprotective effect. The compounds of the invention can be administered singly or together in the form of a novel combination composition, as will be described in more detail below.

Those of skill in the art will appreciate that the compounds of the invention can contain chiral centers and therefore can exist as enantiomers, diastereomers, and racemates. The various huperzine or nicotinic compounds can further exhibit the phenomena of tautomerism, conformational isomerism, positional isomerism, or geometric isomerism. It is to be understood that the compositions and methods of the invention encompass using any stereoisomeric, tautomeric, conformational, and geometric isomeric forms that provide a measurable neuroprotective effect, or mixtures of any of these various isomeric forms. For example, the compositions and methods can employ enantiomers of the various huperzine or nicotinic compounds or mixtures of optically active isomers including, but not limited, to racemic mixtures. For example, one compound of the invention, such as the huperzine compound, can be optically active, while the nicotinic compound, can be a racemic mixture, or vice versa. Unless a specific isomer or mixture is specified, the expressions "huperzine compound" and "nicotinic compound" are intended to encompass all active isomers, tautomers, and mixtures thereof.

When included in the compositions of the invention or employed in the methods of the invention, the compounds of the invention, independently of one another can, where applicable, be in the form of free acids, free bases, or pharmaceutically effective or acceptable salts thereof.

The methods and compositions of the invention can also employ, where applicable, solvated as well as unsolvated forms of the compounds of the invention.

5.3 Synthesis and Sources of Compounds of the Invention

Suitable starting materials for synthesis of huperzine compounds, salts, and hydrates thereof and nicotinic compounds, salts and hydrates thereof can be obtained commercially or through standard chemical syntheses well known by those of skill in the art using commercially available reagents. Where optically active isomers are desired, the optically active compound can be synthesized or isolated using well-known chiral synthetic or separation techniques. Enantiomeric and stereoisomeric mixtures of compounds of the invention can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric-synthetic methods. Additional sources for isolation, synthesis or chiral-specific syntheses or isolation techniques are provided under the appropriate entry of *The Merck Index*, 12$^{th}$ Edition, incorporated herein by reference.

5.3.1 Synthesis and Sources of Huperzine Compounds

Methods for obtaining huperzine compounds, salts, and hydrates thereof suitable for use in the compositions and methods of the invention are well known. For example, the various huperzine compounds can be synthesized according to the methods taught in the patents and references listed in Section 5.1 or this application. Some huperzine compounds, such as (−)- huperzine A and (±)-huperzine A, are available from commercial sources (Sigma Chemical Company, St. Louis, Mo.).

(−)-10,10-Dimethyl huperzine A and (+)-10,10-dimethyl huperzine A can be separated from one another via chiral separation. Briefly, racemic (±)-10,10-dimethyl huperzine A (synthesized according to the method taught in Kozikowski et al., 1996, *Bioorg. Med. Chem. Lett.* 6:259) is resolved into its individual enantiomers by HPLC using a chiral column (e.g., CHIRALPAK AD Column, Daicel Chemical Industries, Ltd.) containing, for example, amylose tris(3,5-dimethylphenyl carbonate) coated on a 10 $\mu$m silica gel substrate and hexanes/ethanol/diethylamine (90/10/0.05) as the eluent. Samples can be prepared in ethanol (about 20 mg/ml) and then diluted with the mobile phase (about 2 ml) prior to injection. A flow rate of 4.0 ml/min. (at room temp.) on a semi-preparative column (25×1.0 cm) utilizing 300 $\mu$l per injection gives good results. The peaks can monitored using UV detection at 230 nm. The retention time is 10.3 min. for the (+)-isomer and 11.0 min. for the (−)-isomer. This method can be routinely adapted for isolating other optically active huperzine compounds.

5.3.2 Synthesis and Sources of Nicotinic Compounds

Methods for obtaining nicotinic compounds, salts, and hydrates thereof suitable for use in the compositions and methods of the invention are well known. The various nicotinic compounds can be synthesized according to the methods taught in the patents and references listed in Section 5.1 of this application. Many nicotinic compounds, such as, (−)-nicotine, (+)-nicotine, cytisine, epibatidine, and anabasine, are available from commercial sources (Sigma Chemical Company, St. Louis, Mo.). Additional sources for isolation, synthesis or chiral-specific syntheses or isolation techniques are provided under the appropriate entry of *The Merck Index*, 12$^{th}$ Edition, incorporated herein by reference.

5.4 Formulation and Routes of Administration

The compounds of the invention can be administered according to the methods of the invention by virtually any mode including, but not limited to, oral, nasal, parenteral, transdermal, and buccal administration, etc. The compounds of the invention can be administered adjunctively, for example, simultaneously or serially in either order. When administered serially, the compounds of the invention should be administered sufficiently close in time so as to provide the desired effect, for example within 1–3 hours, preferably 2, and more preferably within 1 hour of each other. In a particularly convenient embodiment, one or both of the compounds are administered transdermally via a transdermal patch. The compounds can be formulated into separate patches or preferably combined in a single patch.

The compounds can be adjunctively administered therapeutically to treat, prevent, reverse, or slow the rate of onset of neuronal dysfunctions, such as cognitive decline or CNS injury, or prophylactically to either protect against further neuronal dysfunction associated with these processes or to avoid or forestall the onset of neuronal dysfunction altogether. For example, the compositions of the invention can be adjunctively administered prophylactically to healthy subjects to slow or halt the progression of age-related declines in cognition or, depending upon the age of the subject, to avoid age-related declines in cognition altogether. In some instances, the treatment can even enhance or improve cognitive function, particularly memory acquisition, storage or retrieval or concentration (focus). The compositions of the invention are particularly useful for treating, preventing, reversing, or slowing the progression Alzheimer's disease and minimal cognitive impairment.

The compounds of the invention can be adjunctively administered to a subject, including a human, using a wide variety of routes or modes of administration. Suitable routes of administration include, but are not limited to, oral inhalation; nasal inhalation; transdermal; oral; rectal; transmucosal; intestinal; and parenteral administration, including intramuscular, subcutaneous, and intravenous injections. The compounds of the invention can be administered via the same or via a different mode of administration. For example, a huperzine compound, pharmaceutically acceptable salt or hydrate can be administered orally and a nicotinic compound, pharmaceutically acceptable salt or hydrate can be administered via a transdermal patch. Preferably, the compounds of the invention are administered transdermally via a transdermal patch, or the nicotinic compound, pharmaceutically acceptable salt or hydrate is administered transdermally or by nasal inhalation and the huperzine compound, pharmaceutically acceptable salt or hydrate is administered orally.

Various combinations of compounds of the invention can be administered. In addition, the compounds of the invention can be administered in cocktails combined with other therapeutic agents. Of course, the choice of therapeutic agents that can be co-administered with the composition of the invention will depend, in part, on the condition being treated. For example, the compounds of the invention can be administered in cocktails comprising other agents used to treat the pain and other symptoms and side effects commonly associated with neuronal dysfunction, such as cognitive decline and CNS injury. The compounds of the invention can also be administered in cocktails containing other agents that are commonly used to treat the above conditions.

The compounds of the invention can be formulated either as single compounds per se or as mixtures of compounds of the same type (e.g., two different nicotine analogs), or they can be formulated together in the form of a composition. Such compositions will generally comprise a huperzine compound, pharmaceutically acceptable salt or hydrate and a nicotinic compound, pharmaceutically acceptable salt or hydrate, but can comprise one or more huperzine compounds in combination with one or more nicotinic compounds. The formulations will generally include the huperzine and nicotinic compounds and one or more pharmaceutically acceptable carriers, excipients or diluents.

Pharmaceutical compositions for use in accordance with the present invention can be formulated in conventional manner using one or more physiologically acceptable carriers, excipients, diluents or auxiliaries that facilitate processing of the compounds of the invention into compositions of the invention that can be used pharmaceutically. The choice of formulation is dependent upon the selected administration route.

In one convenient embodiment, the compounds of the invention are formulated, either singly or together. Such long acting formulations can be administered by implantation or transcutaneous delivery (for example subcutaneously or intramuscularly), intramuscular injection, or transdermally. Thus, for example, the compounds of the invention can be formulated with suitable polymeric or hydrophobic materials (such as an emulsion in an acceptable oil) or ion exchange resins, or as sparingly soluble derivatives, for example, as a sparingly soluble salt.

The most preferred depot preparations are those that are suitable for transdermal administration, such as a transdermal patch. Patches and formulations suitable for transdermal administration of nicotinic compounds are described in U.S. Pat. Nos. 5,725,876; 5,716,635; 5,633,008; 5,603,947; 5,411,739; 5,364,630; 5,230,896; 5,004,610; 4,943,435; 4,908,213; and 4,839,174, which patents are hereby incorporated herein by reference. As huperzine compounds, pharmaceutically acceptable salts or hydrates are readily absorbed and cross cell membranes and the blood-brain barrier, any of these formulations can be routinely adapted for transdermal administration. Preferably, the compounds of the invention are formulated into a single transdermal patch. The amounts of each compound typically formulated into such patches are described in more detail, below.

For injection, the compounds of the invention can be formulated in physiologically compatible aqueous solutions, such as Hanks's solution, Ringer's solution, or physiological saline buffer. For transmucosal administration, penetrants appropriate to the barrier to be permeated are used in the formulation. Such penetrants are generally known in the art.

For oral administration, the compounds of the invention can be formulated with pharmaceutically acceptable carriers well known in the art. Such carriers enable the compounds of the invention to be formulated for oral administration as tablets, pills, gums dragees, capsules, liquids, gels, syrups, slurries, suspensions and the like. Alternatively, the compounds can be formulated into candies, cookies, or other edible foodstuffs. Pharmaceutical preparations for oral use can be obtained by mixing the compounds of the invention with a solid excipient, optionally grinding the resulting mixture, and processing the mixture of granules, after adding suitable auxiliaries, if desired, to obtain tablets or dragee cores. Suitable excipients include, but are not limited to, fillers, such as sugars, including lactose, sucrose, mannitol, or sorbitol; cellulose preparations, such as maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, such as cross-linked polyvinyl pyrrolidone, agar, or alginic acid or a salt thereof, such as sodium alginate.

Dragee cores are provided with suitable coatings. For this purpose, concentrated sugar solutions can be used that can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the compounds of the invention in an admixture with filler, such as lactose; binders, such as starches; or lubricants, such as talc or magnesium stearate; or stabilizers. In soft capsules, the compounds of the invention can be dissolved or suspended in suitable liquids, such as fatty oils, liquid paraffin, or liquid polyethylene glycols. In addition, stabilizers can be added to the soft-capsule formulation. All formulations for oral administration should be in dosages suitable for such administration.

For buccal administration, the compositions can take the form of oral sprays, tablets, gums, or lozenges formulated by well-known methods.

A candy formulation suitable for oral or buccal administration of nicotinic compounds, pharmaceutically acceptable salts and hydrates is described in U.S. Pat. No. 6,083,962, which is hereby incorporated herein by reference. Additional formulations suitable for oral or buccal administration of nicotinic compounds, pharmaceutically acceptable salts and hydrates are described in U.S. Pat. Nos. 5,939,100; 5,799,633; 5,662,920; 5,603,947; 5,549,906; D358,683; 5,326,563; 5,293,883; 5,147,654; 5,035,252; 4,967,773; 4,907,606; 4,848,376; and 4,776,353, which are hereby incorporated herein by reference. All of these formulations can be routinely adapted for administration of huperzine compounds, pharmaceutically acceptable salts and hydrates.

For administration by oral or nasal inhalation, the compounds of the invention are conveniently delivered in the form of an aerosol spray delivered via pressurized packs or a nebulizer, with a suitable propellant, e.g., carbon dioxide or other suitable gas. In the case of a pressurized aerosol, the dosage unit can be controlled by a dose-metered valve. Capsules and cartridges, e.g. gelatin, for use in an inhaler or insufflator can be formulated as a powder mix of the compounds if the invention and a suitable powder base, such as lactose or starch. Formulations suitable for nasal inhalation of nicotinic compounds, pharmaceutically acceptable salts and hydrates are described in U.S. Pat. Nos. 5,935,604 and 5,564,442, which are hereby incorporated herein by reference. These formulations can be routinely adapted to nasally administer huperzine compounds.

The compounds of the invention can be formulated for parenteral administration by injection, e.g., by bolus injection or continuous infusion. Formulations for injection can be presented in unit-dosage form, e.g., in ampoules or in multi-dose containers, optionally with an added preservative. The compositions can take such forms as suspensions, solutions, or emulsions in oily or aqueous vehicles, and can contain formulatory agents, such as suspending, stabilizing, or dispersing agents.

Pharmaceutical formulations for parenteral administration include aqueous solutions of the compounds of the invention in water-soluble form. Additionally, suspensions of the compounds of the invention can be prepared as appropriate oily-injection suspensions. Suitable lipophilic solvents or vehicles include fatty oils, such as sesame oil, or synthetic-fatty-acid esters, such as ethyl oleate or triglycerides, or liposomes. Aqueous-injection suspensions can contain substances that increase the viscosity of the suspension, such as sodium carboxymethyl cellulose, sorbitol, or dextran. Optionally, the suspension can contain suitable stabilizers or agents that increase the solubility of the compounds of the invention to allow for the preparation of highly concentrated solutions.

Alternatively, the compounds of the invention can be in powder form for constitution with a suitable vehicle, e.g., sterile pyrogen-free water, before use.

The compounds of the invention can also be formulated in rectal compositions, such as suppositories or retention enemas, e.g., containing conventional suppository bases, such as cocoa butter or other glycerides.

The pharmaceutical compositions also can comprise suitable solid- or gel-phase carriers or excipients. Examples of such carriers or excipients include, but are not limited to, calcium carbonate, calcium phosphate, various sugars, starches, cellulose derivatives, gelatin, and polymers, such as polyethylene glycols.

5.5 Effective Dosages

Pharmaceutical preparations suitable for use with the present invention include compositions wherein the compounds of the invention are present in effective amounts, i.e., in amounts effective to achieve the intended purpose, for example, neuroprotection. Of course, the actual amounts of the compounds of the invention effective for a particular application will depend upon a variety of factors including, inter alia, the condition being treated, the age and weight of the subject and, where appropriate, the judgment of the prescribing physician. For example, when administered as a neuroprotectant, such compositions will contain amounts of compounds of the invention effective to provide neuroprotection. When administered to enhance memory, or prevent or reverse memory decline, such compositions will contain amounts of compounds of the invention effective to achieve these results. Determination of effective amounts is well within the capabilities of those skilled in the art, especially in light of the detailed disclosure herein.

The compounds of the invention can be administered adjunctively in any manner that achieves the requisite therapeutic or prophylactic effect. Therapeutically or prophylactically effective doses of the compounds of the invention can be determined from animal or human data for analogous compounds that are known to exhibit similar pharmacological activities, such as huperzine A or nicotine. The applied doses can be adjusted based on the relative bioavailability, potency and in vivo half-life of the administered compounds as compared with these other agents. Applied dosages can also be estimated from in vitro neurotoxicity assays, such as the assays provided in the following Examples.

Adjusting the dose to achieve maximal efficacy in humans based on the methods described above and other methods that are well-known is well within the capabilities of the ordinarily skilled artisan.

Typically, dosages in the range of 0.05 $\mu$g/kg/day to 2000 $\mu$g/kg/day of the huperzine compound, pharmaceutically acceptable salt or hydrate and 1 $\mu$g/kg/day to 2000 $\mu$g/kg/day of the nicotinic compound, pharmaceutically acceptable salt or hydrate are administered as part of a daily regimen, regardless of the mode of administration. Where two or more compounds of each class are administered (e.g., huperzine A and huperzine B), the above-delineated dosage ranges refer to the total dosage of the particular class of compound. Doses for administration of the huperzine compounds, pharmaceutically acceptable salts and hydrates described herein preferably range from about 0.05 to 25 µg/kg/day, more preferably, in the range of about 1 to 5 µg/kg/day. Doses for administration of the nicotinic compounds, pharmaceutically acceptable salts and hydrates described herein preferably range from about 20 to 200 µg/kg/day. Nicotine transdermal patches are available in a variety of nicotine ranges, for example, containing 2.5 mg, 5 mg, 10 mg, 15 mg, and 20 mg of nicotine, are commercially available under several tradenames including, but not limited to, NICOTROL (Pharmacia). These patches can be used in the present methods according to the manufacturer's instructions to achieve an effective dosage. If desirable, the patches can be cut into smaller sizes to lower the dose and avoid adverse side effects. Transdermal patches for daily administration of huperzine compounds, pharmaceutically acceptable salts and hydrates will typically comprise from about 5 µg to 400 µg huperzine compound, pharmaceutically acceptable salt or hydrate. Preferably, a single transdermal patch will include a huperzine compound and a nicotinic compound.

Depending upon the neuroprotective effect desired, the compounds of the invention can be adjunctively administered to achieve either a therapeutic or a prophylactic effect. For example, the compounds of the invention can be prophylactically adjunctively administered to a healthy young, middle-aged or elderly subject who has not yet suffered age-related neuronal dysfunction, such as cognitive decline in order to protect against such declines, or even to therapeutically enhance cognition, including, for example, concentration (focus) or memory acquisition, storage or retrieval. Alternatively, the compounds of the invention can be adjunctively administered to older subjects who have suffered age-related neuronal dysfunction, such as declines in cognitive function, to prophylactically protect against further age-related cognitive decline, or to improve cognitive function.

The compounds of the invention can be adjunctively administered to individuals suffering from neuronal dysfunction, such as cognitive decline characterized by concentration loss, memory-acquisition loss, and information-storage or retrieval loss; neuronal disorders, such as cognitive decline associated with aging and minimal cognitive impairment; severe neurodegenerative disorders, such as Alzheimer's disease; and neuronal dysfunction associated with loss of motor skills, such as Parkinson's disease and amyotrophic lateral sclerosis. The compounds of the invention can also treat, prevent, or reverse neuronal dysfunction resulting from CNS injury, such as stroke, spinal-cord injury, and peripheral-nerve injury. Such adjunctive administration can protect against further neuronal dysfunction and cognitive decline and can improve cognitive function.

Regardless of the condition of the subject, the compounds of the invention are typically adjunctively administered as part of a daily regimen, with daily doses being those previously described.

5.6 Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). The compounds of the invention that exhibit high therapeutic indices are preferred. Therapeutic index data obtained from animal studies can be used in formulating a range of dosages for use in humans. The dosage of such compounds preferably lies within a range of plasma concentrations that include the $ED_{50}$ with little or no toxicity. The dosage can vary within this range depending upon the dosage form employed and the route of administration utilized.

The invention is illustrated by way of working examples that demonstrate the neuroprotective effect of a combination of (−)-huperzine A and (−)-nicotine in two established in vitro models of neurotoxicity. In both models, the combination of (−)-huperzine A and (−)-nicotine provided greater neuroprotection than either agent alone.

6. EXAMPLES

6.1 Example 1

Neuroprotective Effect of (−)-Huperzine A Used Adjunctively with (−)-Nicotine Against NMDA-Induced Cell Toxicity This Example demonstrates the increased neuroprotective effect of adjunctively administered (−)-huperzine A and (−)-nicotine, illustrative compounds of the invention, against NMDA-induced cell toxicity.

6.1.1 Experimental Protocol

In a first experiment, four samples each containing neuronal-glial cultures from mouse cerebral cortical cultures and a different concentration of (−)-nicotine (ranging from 0 to 100 µM) were treated for 10 minutes with 75 µM of NMDA (commercially available, for example, from Sigma Chemical Co., St. Louis, Mo.) to induce cell death. The cultures were prepared from 15-day-old fetal Swiss-Webster mice, as described in Bruno et al., 1998 *Neuroscience* 85:751-7 (hereinafter "Bruno et al."), incorporated herein by reference. Neuronal cells were plated in 96-well plates on a layer of confluent glial cells at a density of 200,000 cells/well in EMEM medium containing 5% fetal bovine serum and 5% horse serum. Then the NMDA was removed replacing the medium with fresh serum-free culture medium and cell death was assessed for each sample by measuring the amount of lactate dehydrogenase ("LDH") released into the medium according to the procedure described in Bruno et al. The data are summarized in FIG. 1, Graph A, as lines connecting the values (represented by unfilled squares) of % of NMDA toxicity (i.e., % cell death) at the corresponding concentration of (−)-nicotine in µM.

In a second experiment, six samples each containing neuronal-glial cultures from mouse brain and a different concentration of (−)-huperzine A (ranging from 0 to 10 µM) were treated with 75 µM of NMDA, using the above-described procedure. Then cell death was assessed for each sample using the procedure described above. The data are summarized in FIG. 1, Graph B, as lines connecting the values (represented by unfilled circles) of % of NMDA toxicity at the corresponding concentration of (−)-huperzine A in µM.

In a third experiment, six samples each containing neuronal-glial cultures from mouse brain, a different concentration of (−)-huperzine A (ranging from 0 to 10 µM), and a fixed concentration of 10 µM of (−)-nicotine were treated with 75 µM NMDA, using the procedure described above. Then cell death was assessed for each sample as above. The data are summarized in FIG. 1, Graph B, as lines connecting the values (represented by black-filled circles) of % of NMDA toxicity at the corresponding µM-concentration of(−)-huperzine A.

6.1.2 Results

FIG. 1 shows that in mouse-brain mixed cortical cultures, NMDA-induced cell death was decreased in a dose-dependent manner by either (−)-nicotine alone (FIG. 1, Graph A, unfilled squares) or (−)-huperzine A alone (FIG. 1, Graph B, unfilled circles). The maximal level of neuroprotection obtained was about 55% (i.e., 45% cell death) with (−)-nicotine alone and about 45% (i.e., 55% cell death) with (−)-huperzine A alone. In stark contrast, when (−)-nicotine and (−)-huperzine A were used adjunctively (FIG. 1, Graph B, black-filled circles) a pronounced increase in neuroprotection over either (−)-huperzine A alone or (−)-nicotine alone, was observed. The effect of 10 μM (−)-nicotine (about 40% neuroprotection when tested alone) was increased by adjunctive use with (−)-huperzine A, reaching a maximal effect of about 70% neuroprotection at 10 μM (−)-huperzine A. These results demonstrate that adjunctive administration of (−)-huperzine A, an illustrative huperzine compound, and (−)-nicotine, an illustrative nicotinic compound, is useful for providing neuroprotection in a subject.

6.2 Example 2

Neuroprotective Effect of (−)-Huperzine A Used Adjunctively with (−)-Nicotine Against β-Amyloid-Peptide-Induced Cell Toxicity This Example demonstrates the increased neuroprotective effect of adjunctively administered (−)-huperzine A and (−)-nicotine, illustrative compounds of the invention, against β-amyloid-peptide-induced cell toxicity cell toxicity.

6.2.1 Experimental Protocol

In a first experiment, four samples each containing cultures of granule neurons prepared from mouse cerebellum and a different concentration of (−)-nicotine (ranging from 0 to 100 μM) were treated for 48 hours with 25 μM β-amyloid peptide ("AP") (commercially available, for example, from Bachem, Inc., Torrance, Calif.) to induce cell death, according to the procedure described in Copani et al., 1995 Mol Pharmacol 47:890-7 (hereinafter "Copani et al.").

Then cell death was assessed by measuring the amount of LDH released into the medium according to the procedure described in Bruno et al. The data are summarized in FIG. 2, Graph A, as lines connecting the values (represented by unfilled squares) of % of β-amyloid-peptide-induced toxicity (i.e., % cell death) at the corresponding concentration of nicotine in μM.

In a second experiment, four samples each containing cultures of granule neurons prepared from mouse cerebellum and a different concentration of (−)-huperzine A (ranging from 0 to 10 μM), were treated for 48 hours with 25 μM AP, (25–35 fragment) according to the above-described procedure. Then cell death was assessed as described above. The data are summarized in FIG. 2, Graph B, as lines connecting the values (represented by unfilled circles) of % of β-amyloid-peptide-induced toxicity at a particular concentration of (−)-huperzine A in μM.

In a third experiment, 4 samples each containing cultures of granule neurons prepared from mouse cerebellum, a different concentrations of (−)-huperzine A (ranging from 0 to 10 μM), and a fixed concentration of 10 μM of (−)-nicotine were treated for 48 hours with 25 μM AP using the procedure described above. Then cell death was assessed as above. The data are summarized in FIG. 2, Graph B, as lines connecting the values (represented by black-filled circles) of % of β-amyloid-peptide-induced toxicity at a particular μM-concentration of (−)-huperzine A.

6.2.2 Results

FIG. 2 shows that in cultures of granule neurons prepared from mouse cerebellum, the toxicity induced by a long-term application of 25 μM AP was decreased in a dose-dependent manner by either (−)-nicotine alone (FIG. 2, Graph A, unfilled squares) or (−)-huperzine A alone (FIG. 2, Graph B, unfilled circles). The maximal level of neuroprotection was about 55% (i.e., 45% cell death) with (−)-nicotine alone and about 30% (i.e., 70% cell death) with (−)-huperzine A alone. In stark contrast, when (−)-nicotine and (−)-huperzine A were used adjunctively (FIG. 2, Graph B, black-filled circles) a pronounced increase in neuroprotection over either (−)-huperzine A alone or (−)-nicotine alone, was observed. The effect of 10 μM (−)-nicotine (about 20% neuroprotection when tested alone) was increased by adjunctive use with (−)-huperzine A, reaching a maximal effect of about 80% neuroprotection at 10 μM (−)-huperzine A. These results demonstrate that adjunctive administration of (−)-huperzine A, an illustrative huperzine compound, and (−)-nicotine, an illustrative nicotinic compound, is useful for providing neuroprotection in a subject.

6.3. Example 3

Neuroprotective Effect of (−)-Huperzine A Used Adjunctively with (−)-Nicotine Against NMDA-induced Cell Toxicity This Example demonstrates the synergistic neuroprotective effect of compositions of the invention against NMDA-induced cell toxicity relative to huperzine compounds alone or nicotine compounds alone, measured using an in vitro model. The synergistic effect was observed through the use of low concentrations of (−)-nicotine and (−)-huperzine A.

6.3.1 Experimental Protocol

In a first experiment, 5 samples each containing neuronal-glial cultures from mouse cerebral cortical cultures (prepared as described above in Section 6.1.1) and a different concentration of (−)-huperzine A (ranging from 0 to 1000 nM) were treated for 10 minutes with 100 μM of NMDA to induce cell death, according to the procedure described in Bruno et al. Then the NMDA was removed and cell death was assessed for each sample by measuring the amount of LDH released into the medium according to the procedure described in Bruno et al The data are summarized in FIG. 3 as lines connecting the values (represented by unfilled circles) of % of NMDA toxicity at the corresponding concentration of (−)-huperzine A in nM.

In a second experiment, six samples each containing neuronal-glial cultures from mouse cerebral cortical cultures, a different concentration of (−)-huperzine A (ranging from 0 to 1000 μM), and a fixed concentration of 0.1 μM of (−)-nicotine were treated with 100 μM NMDA, using the procedure described above. Then cell death was assessed for each sample as above. The data are summarized in FIG. 3 as lines connecting the values (represented by black-filled circles) of % of NMDA toxicity at the corresponding nM-concentration of (−)-huperzine A.

6.3.2 Results (−)-Huperzine A alone, used in the range of 1–1000 nM, produced no significant neuroprotective effects; however, it enhanced the effect of 0.1 μM (−)-nicotine in a dose-dependent manner. 0.1 μM of (−)-nicotine had little effect in the absence of (−)-huperzine A. Significantly, however, 0.1 μM of (−)-nicotine resulted in about 70% neuroprotection in presence of 1000 μM (i.e., 1 μM) (−)-huperzine A. These results demonstrate that adjunctive administration of (−)-huperzine A, an illustrative huperzine compound, and (−)-nicotine, an illustrative nicotinic compound, is useful for providing neuroprotection in a subject.

The present invention is not to be limited in scope by the specific embodiments disclosed in the examples, which are intended as illustrations of a few aspects of the invention, and any embodiments that are functionally equivalent are within the scope of this invention. Indeed, various modifications of the invention in addition to those shown and described herein will become apparent to those skilled in the art and are intended to fall within the scope of the appended claims.

All cited references are hereby incorporated herein in their entireties by reference.

What is claimed is:

1. A composition comprising a huperzine compound or a pharmaceutically acceptable salt or hydrate thereof and a nicotinic compound or pharmaceutically acceptable salt or hydrate thereof.

2. The composition of claim 1, wherein the huperzine compound is (−)-huperzine A, (+)-huperzine A, (±)-huperzine A, (−)-huperzine B, (+)-huperzine B, or (±)-huperzine B.

3. The composition of claim 1, wherein the huperzine compound is a derivative or analog of huperzine A or huperzine B.

4. The composition of claim 3, wherein the huperzine A analog is a C-10 huperzine A analog.

5. The composition of claim 4, wherein the C-10 huperzine A analog is (+)-10-methyl huperzine A, (−)-10-methyl huperzine A, (±)-10-methyl huperzine A, (+)-10,10-dimethyl huperzine A, (−)-10,10-dimethyl huperzine A, or (±)-10,10-dimethyl huperzine A.

6. The composition of claim 1, wherein the nicotinic compound is (+)-nicotine, (−)-nicotine, or (±)-nicotine.

7. The composition of claim 1, wherein the nicotinic compound is an analog or derivative of nicotine.

8. The composition of claim 1, wherein the nicotinic compound is epibatidine, cytisine, lobeline, or anabasine or an analog or a derivative thereof or pharmaceutically acceptable salt or hydrate thereof.

9. The composition of claim 1, wherein the huperzine compound is huperzine A or a C-10 huperzine A analog and the nicotinic compound is nicotine, epibatidine, cytisine, lobeline, or anabasine.

10. The composition of claim 1, wherein the huperzine compound is (−)-huperzine A, (±)-huperzine A, (+)-10,10-dimethyl huperzine A, (−)-10,10-dimethyl huperzine A, (±)-10,10-dimethyl huperzine A, (+)-10-methyl huperzine A, (−)-10-methyl huperzine A, or (±)-10-methyl huperzine A and the nicotinic compound is (+)-nicotine, (−)-nicotine, or (±)-nicotine.

11. The composition of claim 1, wherein the huperzine compound is (−)-huperzine A and the nicotinic compound is (−)-nicotine.

12. The composition of claim 1, further comprising a pharmaceutically acceptable carrier, excipient, or diluent.

13. A transdermal patch containing the composition of claim 1.

14. A method of providing neuroprotection in a subject, said method comprising adjunctively administering to a subject in need thereof an effective amount of a huperzine compound or a pharmaceutically acceptable salt or hydrate thereof and an effective amount of a nicotinic compound or pharmaceutically acceptable salt or hydrate thereof.

15. The method of claim 14, wherein the huperzine compound and the nicotinic compound are administered to the subject simultaneously.

16. The method of claim 14, wherein the huperzine compound and the nicotinic compound are administered to the subject serially.

17. The method of claim 14, wherein the huperzine compound is (−)-huperzine A, (+)-huperzine A, (±)-huperzine A, (−)-huperzine B, (+)-huperzine B, or (±)-huperzine B.

18. The method of claim 14, wherein the huperzine compound is an analog or a derivative of huperzine A or huperzine B.

19. The method of claim 18, wherein the huperzine A analog is a C-10 huperzine A analog.

20. The method of claim 19, wherein the C-10 huperzine A analog is (+)-10-methyl huperzine A, (−)-10-methyl huperzine A, (±)-10-methyl huperzine A, (+)-10,10-dimethyl huperzine A, (−)-10,10-dimethyl huperzine A, or (+)-10,10-dimethyl huperzine A.

21. The method of claim 14, wherein the nicotinic compound is (+)-nicotine, (−)-nicotine, or (±)-nicotine.

22. The method of claim 14, wherein the nicotinic compound is an analog or derivative of nicotine.

23. The method of claim 14, wherein the nicotinic compound is epibatidine, cytisine, lobeline, or anabasine or an analog or a derivative thereof or pharmaceutically acceptable salt or hydrate thereof.

24. The method of claim 14, wherein the huperzine compound is huperzine A or a C-10 huperzine A analog and the nicotinic compound is nicotine, epibatidine, cytisine, lobeline, or anabasine.

25. The method of claim 14, wherein the huperzine compound is (−)-huperzine A, (±)-huperzine A, (+)-10,10-dimethyl huperzine A, (−)-10,10-dimethyl huperzine A, (±)-10,10-dimethyl huperzine A, (+)-10-methyl huperzine A, (−)-10-methyl huperzine A, or (±)-10-methyl huperzine A and the nicotinic compound is (+)-nicotine, (−)-nicotine, or (±)-nicotine.

26. The method of claim 14, wherein the huperzine compound is (−)-huperzine A and the nicotinic compound is (−)-nicotine.

27. The method of claim 14, wherein the huperzine compound and the nicotinic compound are administered together with a pharmaceutically acceptable carrier, excipient, or diluent.

28. The method of claim 14, wherein the huperzine compound and the nicotinic compound are administered via a transdermal patch.

29. A method for treating, preventing, or reversing a neuronal dysfunction, comprising adjunctively administering to a patient in need thereof an effective amount of a huperzine compound, pharmaceutically acceptable salt or hydrate thereof and an effective amount of a nicotinic compound, pharmaceutically acceptable salt or hydrate thereof.

30. The method of claim 29, wherein the huperzine compound and the nicotinic compound are administered to the subject simultaneously.

31. The method of claim 29, wherein the huperzine compound and the nicotinic compound are administered to the subject serially.

32. The method of claim 29, wherein the huperzine compound is (−)-huperzine A, (+)-huperzine A, (±)-huperzine A, (−)-huperzine B, (+)-huperzine B, or (±)-huperzine B.

33. The method of claim 29, wherein the huperzine compound is an analog or a derivative of huperzine A or huperzine B.

34. The method of claim 33, wherein the huperzine A analog is a C-10 huperzine A analog.

35. The method of claim 34, wherein the C-10 huperzine A analog is (+)-10-methyl huperzine A, (−)-10-methyl huperzine A, (±)-10-methyl huperzine A, (+)-10,10-dimethyl huperzine A, (−)-10,10-dimethyl huperzine A, or (±)-10,10-dimethyl huperzine A.

36. The method of claim 29, wherein the nicotinic compound is (+)-nicotine, (−)-nicotine, or (±)-nicotine.

37. The method of claim 29, wherein the nicotinic compound is an analog or derivative of nicotine.

38. The method of claim 29, wherein the nicotinic compound is epibatidine, cytisine, lobeline, or anabasine or an analog or a derivative thereof or pharmaceutically acceptable salt or hydrate thereof.

39. The method of claim 29, wherein the huperzine compound is huperzine A or a C-10 huperzine A analog and the nicotinic compound is nicotine, epibatidine, cytisine, lobeline, or anabasine.

40. The method of claim 29, wherein the huperzine compound is (−)-huperzine A, (±)-huperzine A, (+)-10,10-dimethyl huperzine A, (−)-10,10-dimethyl huperzine A, (±)-10,10-dimethyl huperzine A, (+)-10-methyl huperzine A, (−)-10-methyl huperzine A, or (±)-10-methyl huperzine A and the nicotinic compound is (+)-nicotine, (−)-nicotine, or (±)-nicotine.

41. The method of claim 29, wherein the huperzine compound is (−)-huperzine A and the nicotinic compound is (−)-nicotine.

42. The method of claim 29, wherein the huperzine compound and the nicotinic compound are administered together with a pharmaceutically acceptable carrier, excipient, or diluent.

43. The method of claim 29, wherein the huperzine compound and the nicotinic compound are administered via a transdermal patch.

44. A method for treating, preventing, or reversing concentration loss, memory-acquisition loss, information-storage or retrieval loss, cognitive decline associated with aging, minimal cognitive impairment, Alzheimer's disease, Parkinson's disease, amyotrophic lateral sclerosis, stroke, spinal-cord injury, or peripheral-nerve injury, comprising adjunctively administering to a patient in need thereof an effective amount of a huperzine compound, pharmaceutically acceptable salt or hydrate thereof and an effective amount of a nicotinic compound, pharmaceutically acceptable salt or hydrate thereof.

45. The method of claim 44, wherein the huperzine compound and the nicotinic compound are administered to the subject simultaneously.

46. The method of claim 44, wherein the huperzine compound and the nicotinic compound are administered to the subject serially.

47. The method of claim 44, wherein the huperzine compound is (−)-huperzine A, (+)-huperzine A, (±)-huperzine A, (−)-huperzine B, (+)-huperzine B, or (±)-huperzine B.

48. The method of claim 44, wherein the huperzine compound is an analog or a derivative of huperzine A or huperzine B.

49. The method of claim 48, wherein the huperzine A analog is a C-10 huperzine A analog.

50. The method of claim 49, wherein the C-10 huperzine A analog is (+)-10-methyl huperzine A, (−)-10-methyl huperzine A, (±)-10-methyl huperzine A, (+)-10,10-dimethyl huperzine A, (−)-10,10-dimethyl huperzine A, or (±)-10,10-dimethyl huperzine A.

51. The method of claim 44, wherein the nicotinic compound is (+)-nicotine, (−)-nicotine, or (±)-nicotine.

52. The method of claim 44, wherein the nicotinic compound is an analog or derivative of nicotine.

53. The method of claim 44, wherein the nicotinic compound is epibatidine, cytisine, lobeline, or anabasine or an analog or a derivative thereof or pharmaceutically acceptable salt or hydrate thereof.

54. The method of claim 44, wherein the huperzine compound is huperzine A or a C-10 huperzine A analog and the nicotinic compound is nicotine, epibatidine, cytisine, lobeline, or anabasine.

55. The method of claim 44, wherein the huperzine compound is (−)-huperzine A, (±)-huperzine A, (+)-10,10-dimethyl huperzine A, (−)-10,10-dimethyl huperzine A, (±)-10,10-dimethyl huperzine A, (+)-10-methyl huperzine A, (−)-10-methyl huperzine A, or (±)-10-methyl huperzine A and the nicotinic compound is (+)-nicotine, (−)-nicotine, or (±)-nicotine.

56. The method of claim 44, wherein the huperzine compound is (−)-huperzine A and the nicotinic compound is (−)-nicotine.

57. The method of claim 44, wherein the huperzine compound and the nicotinic compound are administered together with a pharmaceutically acceptable carrier, excipient, or diluent.

58. The method of claim 44, wherein the huperzine compound and the nicotinic compound are administered via a transdermal patch.

* * * * *

UNITED STATES PATENT AND TRADEMARK OFFICE
CERTIFICATE OF CORRECTION

PATENT NO. : 6,369,052 B1
DATED : April 9, 2002
INVENTOR(S) : Kellar et al.

It is certified that error appears in the above-identified patent and that said Letters Patent is hereby corrected as shown below:

Column 22,
Line 14, thereof, please replace "(+)-10,10-dimethyl huperzine A" with -- (±)-10,10-dimethyl huperzine A --.

Signed and Sealed this

Twenty-ninth Day of October, 2002

Attest:

Attesting Officer

JAMES E. ROGAN
Director of the United States Patent and Trademark Office